US00RE43595E

(19) United States
(12) Reissued Patent
Lederer

(10) Patent Number: US RE43,595 E
(45) Date of Reissued Patent: Aug. 21, 2012

(54) NOISE ATTENUATING HEADSET

(76) Inventor: Wayne Lederer, Atlantic Beach, NY (US)

(21) Appl. No.: 13/037,108

(22) Filed: Feb. 28, 2011

Related U.S. Patent Documents

Reissue of:
(64) Patent No.: 7,609,844
Issued: Oct. 27, 2009
Appl. No.: 11/851,860
Filed: Sep. 7, 2007

U.S. Applications:
(62) Division of application No. 10/723,774, filed on Nov. 26, 2003, now Pat. No. 7,292,704.

(60) Provisional application No. 60/516,482, filed on Oct. 31, 2003, provisional application No. 60/515,041, filed on Oct. 28, 2003, provisional application No. 60/514,802, filed on Oct. 27, 2003, provisional application No. 60/514,796, filed on Oct. 27, 2003.

(51) Int. Cl.
*H04R 25/00* (2006.01)

(52) U.S. Cl. ..... 381/380; 381/382

(58) Field of Classification Search ..... 381/67, 381/311, 328, 334, 380, 382; 181/129–131; 600/410, 418, 421, 424, 427
See application file for complete search history.

(56) References Cited

U.S. PATENT DOCUMENTS

| | | | |
|---|---|---|---|
| 3,080,011 | A | 3/1963 | Henderson |
| 3,123,069 | A | 3/1964 | Laisne |
| 3,157,245 | A | 11/1964 | Bernstein |
| 3,306,991 | A | 2/1967 | Wood |
| 3,539,031 | A | 11/1970 | Scanlon |
| 3,667,569 | A | 6/1972 | Mackey |
| 3,730,290 | A | 5/1973 | Scanlon |
| 3,790,712 | A | 2/1974 | Andries |
| 4,261,432 | A | 4/1981 | Gunterman |
| 4,302,635 | A | 11/1981 | Jacobson |
| 4,347,911 | A | 9/1982 | Bertagna |
| 4,439,645 | A | 3/1984 | Scalzo |
| 4,554,993 | A | 11/1985 | Houng |
| 4,701,952 | A | 10/1987 | Taylor |
| 4,864,610 | A | 9/1989 | Stevens |
| 4,880,076 | A | 11/1989 | Ahlberg |
| 4,933,981 | A | 6/1990 | Lederer |
| 4,965,836 | A | 10/1990 | Andre |
| 5,002,151 | A | 3/1991 | Oliveira |
| 5,277,184 | A | 1/1994 | Messana |

(Continued)

OTHER PUBLICATIONS

Skopec, M., "A Primer on Medical Device Interactions with Magnetic Resonance Imaging Systems," U.S. Food and Drug Administration (http://www.fda.gov/cdrh/ode/primer16.html), CDRH pp. 1-16, 1997.

(Continued)

*Primary Examiner* — Davetta W Goins
*Assistant Examiner* — Matthew Eason
(74) *Attorney, Agent, or Firm* — Fish & Richardson P.C.

(57) ABSTRACT

Systems and techniques are disclosed for a headset that may be used in an audio system used in a magnetic field. In one aspect, the system includes an inner set portion adapted to fit into an ear canal. A pneumatic port is disposed in the hole to couple audible sounds to the ear canal. The system may include a non-magnetic transducer coupled to the pneumatic port. The system also may include a fiber-optic microphone to couple sound from a user of the headset. Other techniques provide a stethoscope-type yoke to couple the pneumatic port and the fiber-optic antenna to the non-magnetic transducer.

39 Claims, 4 Drawing Sheets

U.S. PATENT DOCUMENTS

| | | | |
|---|---|---|---|
| 5,313,945 | A | 5/1994 | Friedlander |
| 5,412,419 | A | 5/1995 | Ziarati |
| 5,427,102 | A | 6/1995 | Shimode |
| 5,539,831 | A | 7/1996 | Harley |
| 5,577,504 | A | 11/1996 | Salloway |
| 5,613,222 | A | 3/1997 | Guenther |
| 5,627,902 | A | 5/1997 | Ziarati |
| 5,821,748 | A | 10/1998 | Gatehouse |
| 5,920,636 | A | 7/1999 | Oliveira |
| 5,990,680 | A | 11/1999 | Mansfield |
| 6,310,961 | B1 | 10/2001 | Oliveira |
| 6,463,316 | B1 | 10/2002 | Brungart |
| 6,466,681 | B1 | 10/2002 | Siska |
| 6,741,719 | B1 | 5/2004 | Orten |
| 7,236,605 | B2 | 6/2007 | Oliveira |
| 7,292,704 | B2 | 11/2007 | Lederer |
| 2003/0051939 | A1 | 3/2003 | Werblud |
| 2006/0123527 | A1 | 6/2006 | Porzelt |

OTHER PUBLICATIONS

Newmatic Sound Systems Product Description and Pricing Guide for calendar year 2000.

http://web/archive.org/web/20020603231154/www.newmaticsound.com/headsets/fephs.htm; page from Newmatic Sound Systems on-line catalog for 2000.

Order Granting Request for Ex Parte Reexamination regarding USPN 7,609,844, Control No. 90/011,133, mailed Oct. 25, 2010.

Newmatic Sound Systems Catalog for1998 (2 pages).

Peltor Communications Hearplugs Catalog for 2002 (2 pages).

NOISE ATTENUATING HEADSET

Matter enclosed in heavy brackets [ ] appears in the original patent but forms no part of this reissue specification; matter printed in italics indicates the additions made by reissue.

CROSS REFERENCE TO RELATED APPLICATIONS

This application is a divisional of U.S. Ser. No. 10/723,774, filed on Nov. 26, 2003 *now U.S. Pat. No. 7,292,704*, which in turn claims the benefit of priority from U.S. Provisional Application No. 60/514,482 filed Oct. 31, 2003; U.S. Provisional Application No. 60/515,041, filed Oct. 28, 2003; U.S. Provisional Application No. 60/514,802, filed Oct. 27, 2003; and U.S. Provisional Application No. 60/514,796, filed Oct. 27, 2003 all of which are incorporated herein by reference in their entirety.

BACKGROUND

This disclosure relates to noise-attenuating headsets for use in magnetic fields. Magnetic resonance imaging systems (MRI) produce loud noises associated with the drive pulses applied to the gradient coils. As MRI technology has advanced and the gradient coils have become more powerful, the level of the sound produced has increased to a point where it may be necessary to provide sound pressure protection for people in the vicinity of the MRI system when the system is operating.

SUMMARY

The present application describes systems and techniques relating to noise reduction headsets in a magnetic environment.

The technique includes a magnetically inert headset comprising an outer set portion disposed in an ear cup adapted to cover an ear. An ear insert having a through-hole is disposed in the outer set portion, wherein the inner set portion is adapted to fit into an ear canal. A pneumatic port is disposed in the hole in the inner set to couple audible sound waves to the ear canal.

In an implementation, the technique is facilitated by including a stethoscope-type yoke to couple the pneumatic port to a non-magnetic audio transducer.

In another implementation, the technique is facilitated by including a non-magnetic microphone to enable a user of the headset to communicate with another person. The non-magnetic microphone may be a fiber-optic microphone or a piezoelectric microphone.

In another aspect, the technique includes inserting an ear insert having a through-hole into a ear canal of a user; disposing a pneumatic port into the hole in the ear insert; coupling the pneumatic port to a pneumatic tube; and coupling the pneumatic tube to an output of an audio transducer.

Some implementations of the systems and techniques described herein may provide one or more of the following advantages. The system may reduce the sound level due to the operation of a magnetic device such as a magnetic resource imaging system from entering a user's ear canal. The technique may enable communication to a user in a noisy environment and, in some implementations, enable the user to communicate with another person.

Details of one or more implementations are set forth in the accompanying drawings and the description below. Other features and advantages may be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

The systems and techniques disclosed here relate a system for reducing noise in a headset used in a magnetic environment. For example, MRI systems can produce loud noises associated with drive pulses applied to the MRI gradient coils. A headset may be used to decrease the level of sound that a person hears while undergoing examination in, or in the vicinity of, the MRI system when the system is operating. The headset also may enable a user, such as a patient undergoing an MRI examination, to hear a MRI technologist while the MRI system is operating. The headset can be made of non-magnetic materials and includes an ear insert that may be inserted into an ear canal to reduce the sounds heard by the user.

Figure 1A:
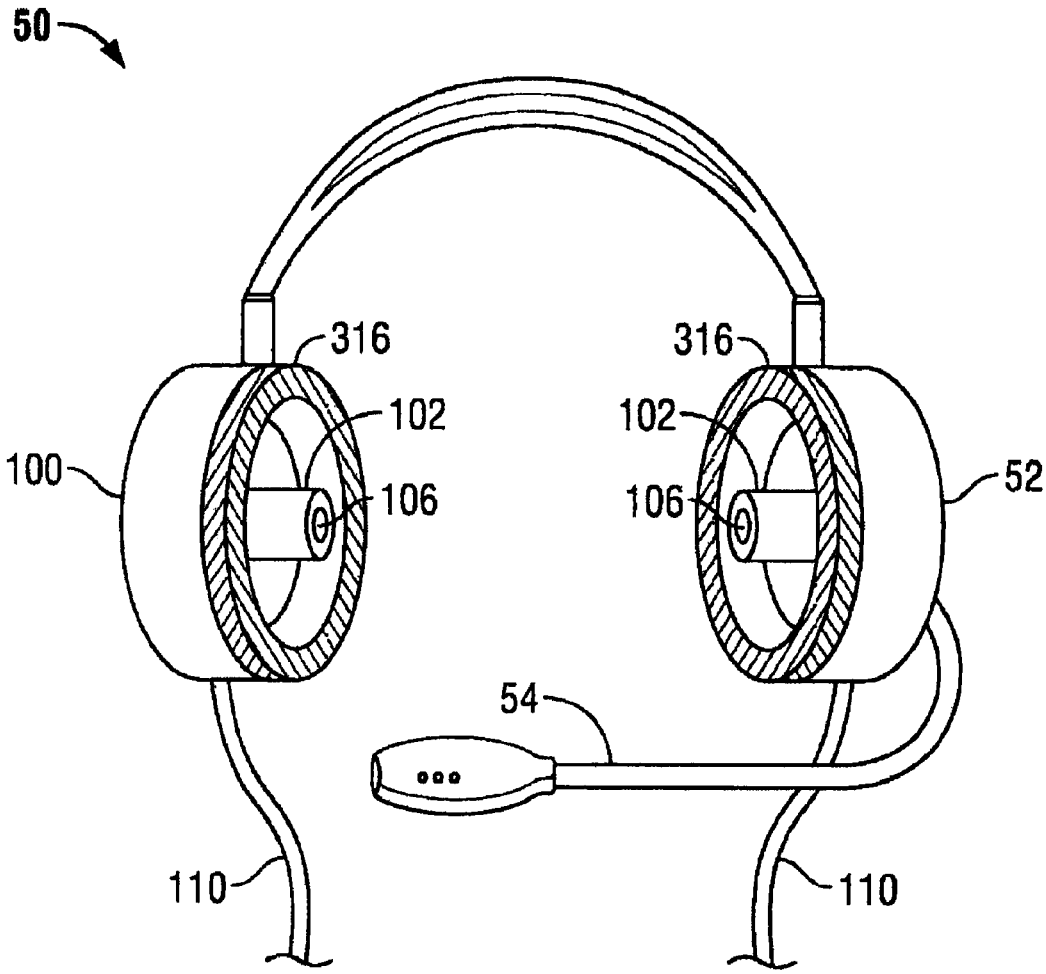
FIGS. 1A-B are illustrations of a first embodiment of the disclosed technique.

FIG. 1A illustrates a noise-attenuating headset 50. The headset includes right and left ear covers 100, 52, respectively, which may have foam padding 316 to attenuate noise and cushion the ear covers when in use. A respective ear insert 102 is disposed in each ear cover. The ear insert is adapted to fit into an ear canal of a user. The ear insert may include a pneumatic port 106 to couple sound received through pneumatic tubes 110. A non-magnetic microphone 54 may be provided for on the headset. The microphone may be used to permit a user to communicate with another person.

Figure 1B:
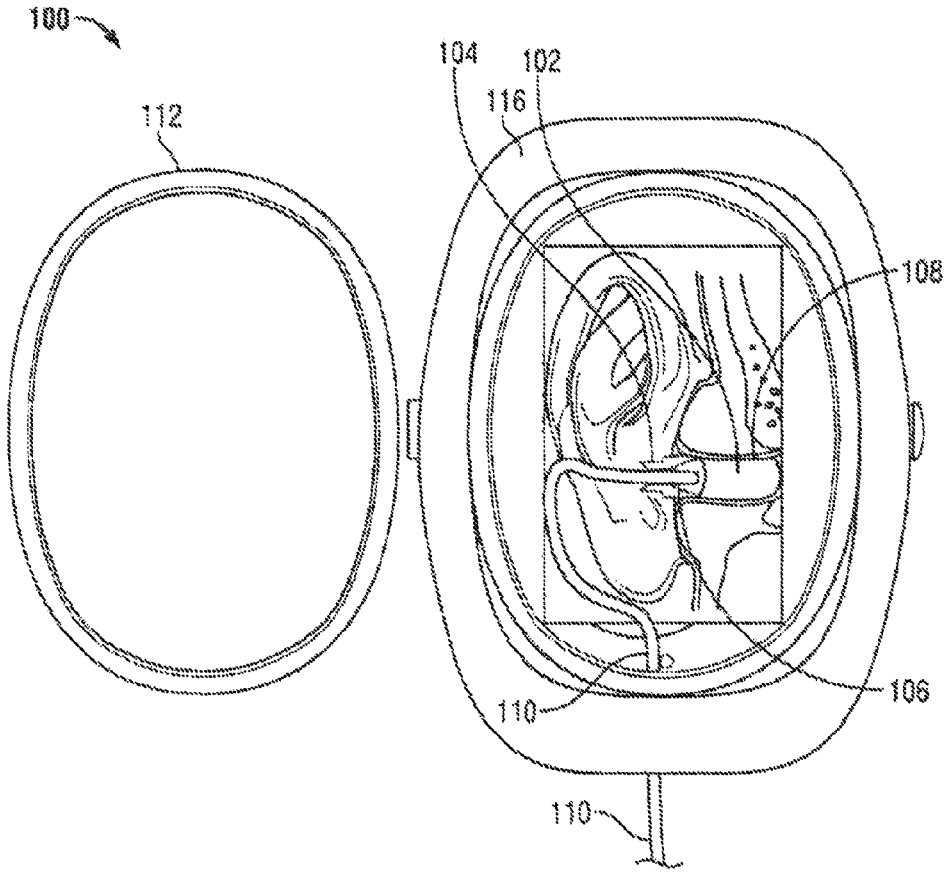

FIG. 1B illustrates the right-side ear cover 100. The left-side may be similarly structured. The headset may be made of non-magnetic materials that are not affected by a magnetic field. The headset includes an inner set portion that may include the ear insert 102 and the pneumatic port 106. The ear insert is adapted to fit into a person's ear canal 108. In an implementation, the ear insert may be made of a material that can conform to the shape of the ear canal upon insertion therein such as compressible foam, vinyl, plastic or rubber. The ear insert may be made in alternative sizes, shapes or materials to conform to the variations in ear canal geometry of different users. Placing the insert within the ear canal so that it substantially conforms to the shape of the ear canal can attenuate the noises that may be created by the gradient coils of a MRI system. An adapter 104 may be used to support the pneumatic port and can couple the port to pneumatic tubing 110. The pneumatic tubing 110 can be used to carry sounds from the output of an audio transducer (not shown). The inner set portion may be disposed within an outer set portion, which includes an ear cup 116. The ear cup 116 may come in different sizes to accommodate different sizes of ears. In an implementation, the ear cup 116 may be provided with a removable access piece 112 to provide access to the inner set portion through an outer surface of the ear cup 116.

Figure 2:
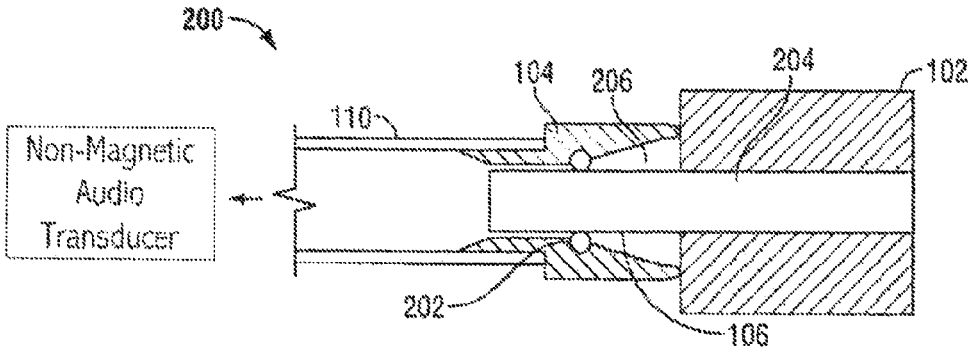
FIG. 2 is an implementation of an inner set portion.

FIG. 2 illustrates an implementation of an inner set portion 200 comprising the ear insert 102 and the pneumatic port 106. The ear insert 102 has a through-hole 204. The pneumatic port 106 may be in the form of a hollow tube and disposed within the ear insert hole 204. The pneumatic port 106 can provide coupling of sound to the ear canal without substantially disturbing the contact between the ear insert and ear canal walls. In an implementation, the ear insert 102 may be intended for disposal after each use for various reasons such as for sanitary purposes. The adapter 104 may be used to couple the pneumatic port 106 to the pneumatic tube 110. In an implementation, the adapter may have a conical opening 206 to help guide the pneumatic port 106 into the pneumatic tube 110. The adapter may comprise a gasket 202 such as an O-ring disposed in the adapter to support, retain or help seal the pneumatic port 106 in the adapter 104.

In an implementation, a non-magnetic microphone may be coupled to the headset to enable communication between the headset wearer and another person. For example, in a MRI system, a user may wear the headset and communicate with the system operator. Non-magnetic microphones include noise-canceling fiber-optic and piezoelectric microphones. The microphone may be coupled to the headset by a non-magnetic mount. An optical fiber associated with the microphone may be routed adjacent the pneumatic tubes to provide connection to the microphone.

The pneumatic port 106 may be placed in the hole 204 of the ear insert 102. A first end of the pneumatic tubing 110 may be coupled to the pneumatic port 106. A second end of the pneumatic tubing may be coupled the output of an audio transducer (not shown). The audio transducer may be located in the magnet room of a MRI system. The ear insert 102 may be disposed in the ear canal. In an implementation, there is an adapter 104 having a conical opening on a first end. The conical adapter is disposed within the ear cup 116 such that when the headset is placed over the ears, the conical opening guides the pneumatic port 106 into the pneumatic tubing 110. The integrity of the coupling of the pneumatic port through the conical adapter to the pneumatic tubing 110 may be verified through the removable access piece 112. The removable piece then may be closed to help keep unwanted noise from the ear.

Figure 3:
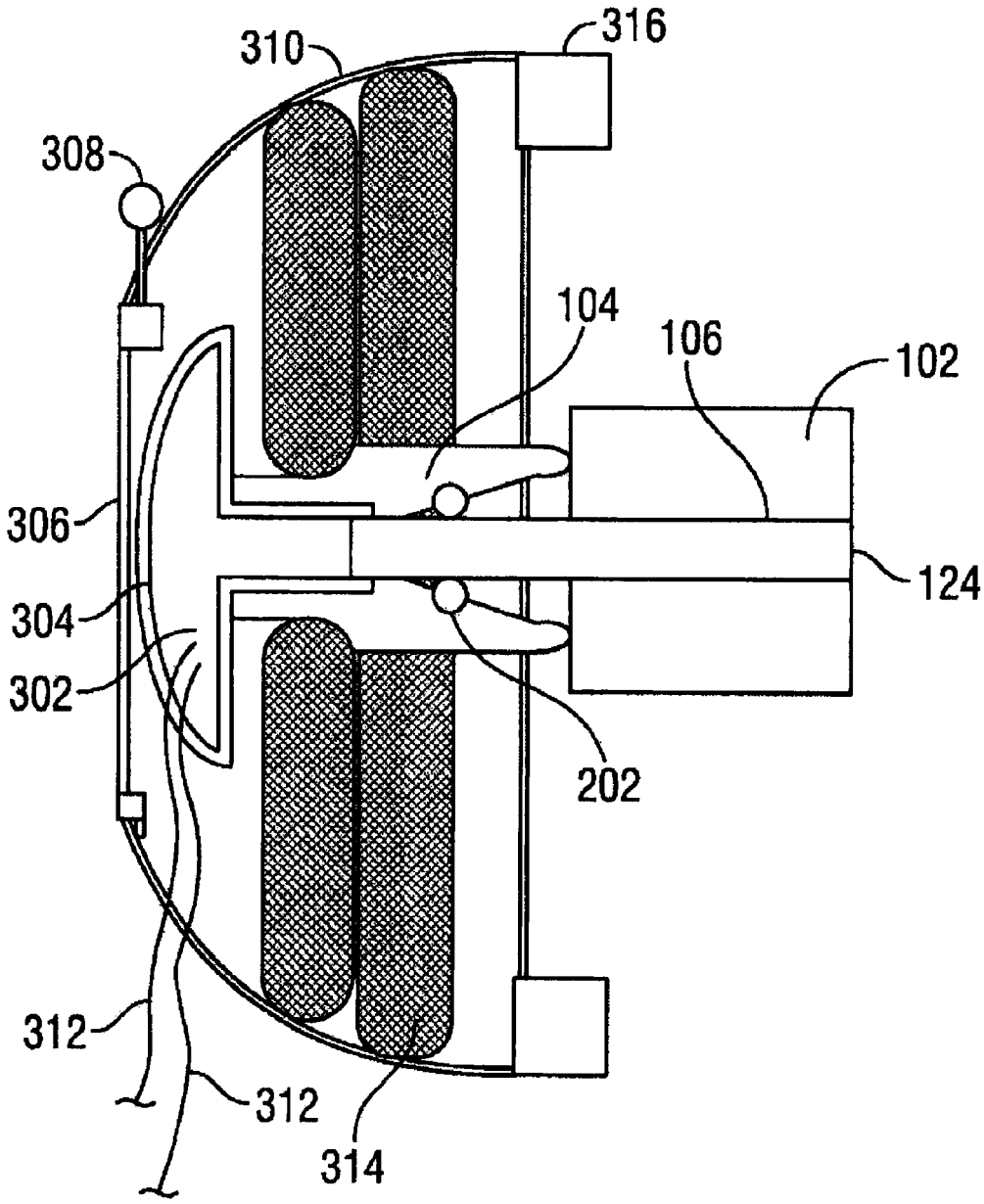
FIG. 3 is an implementation of the noise attenuation technique with a piezoelectric transducer.

FIG. 3 illustrates an implementation of the noise attenuating technique using a piezoelectric transducer. Previously described features will only be repeated as necessary. An ear cup 310 is adapted to fit over an ear. A pad 316 is attached to the ear cup to provide a cushion for the user of the headset and to help dampen sounds. The cushion may be made, for example, of a foam material. A sound absorbing foam 314 may be disposed inside the ear cup 310. A piezoelectric transducer includes a piezoelectric substrate 302 disposed in a piezoelectric enclosure 304. The audio output of an audio transducer (not shown) may be coupled by wires 312 to the piezoelectric transducer, which, in turn, may couple the audio output to the pneumatic port 106 and then through the ear insert that is inserted into the ear canal. The adapter 104 can be used to retain both the pneumatic port and the piezoelectric transducer in proximity with one another. In an implementation, a removable access piece 306 can provide an opening in the ear cup to provide access to the piezoelectric transducer 306, adapter 104, pneumatic port 106 and ear insert 102.

Figure 4:
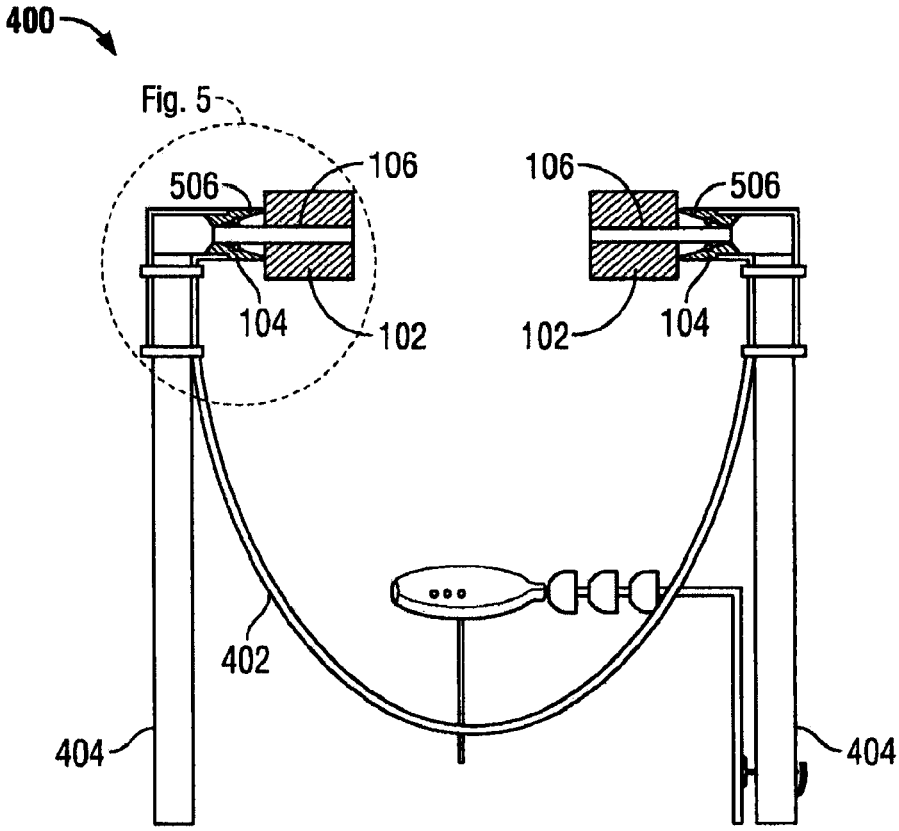
FIG. 4 is an implementation of the noise attenuation technique in a stethoscope-type headset.

FIG. 4 is an implementation of the noise attenuating technique in a stethoscope-type headset assembly 400. *In some implementations, the headset is arranged to provide at least approximately 35 decibels of acoustic attenuation.* As described above, ear inserts 102 are inserted into the ear canal. The stethoscope-type assembly, through pneumatic tubing 404, couples output sounds from an audio transducer (not shown) to the pneumatic ports 106. A stethoscope tubing support 402 may hold the pneumatic tubes 404 together and may be made of a semi-rigid material that can provide a spring pressure to urge the ear inserts 102 into the ear canal. Ear inserts 102 have a through-hole and are adapted to fit into an ear canal. *The headset is arranged to provide a near-hermetic seal between the ear insert 102 and an ear canal wall.* The pneumatic port 106 is disposed in the through-hole. *The pneumatic port 106 is configured to be positioned inside of the ear canal during operation of the headset.* Adapters 506 may be used to guide the pneumatic ports 106 into the pneumatic tubes 404. The stethoscope assembly may protrude from the user's head less than a headset using an ear cup. This type of assembly may be appropriate for users having a large head or ears that do not fit in available ear cups.

Figure 5:
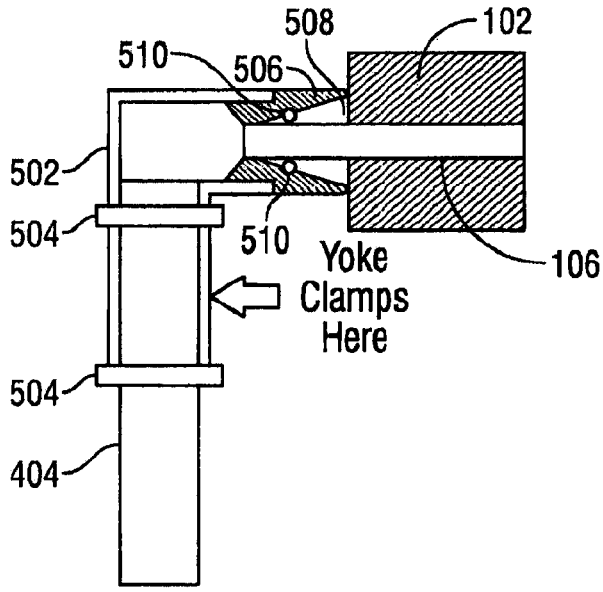
FIG. 5 is a detail view of the yoke attachment of the stethoscope-type headset of FIG. 4.

FIG. 5 is a detail view of the attachment of the pneumatic tube 404 to the pneumatic port 106. The adapter 506 may be used to couple the pneumatic port 106 to the pneumatic tube 404. In an implementation, the adapter may have a conical opening on a first end 508 to help guide and support the pneumatic port 106 into a yoke connector 502. The adapter may comprise a gasket 510 such as an O-ring disposed in the adapter to support, retain or help seal the pneumatic port 106 in the adapter 506. A second end of the adapter 506 is sized to fit snugly into a first end of the yoke connector 502 so as to reduce sound losses in the connection. Other connection arrangements may be used. The yoke connector 502 has a right-angle bend so as to reduce the distance that the stethoscope-type headset protrudes from the user's head. The pneumatic tube 404 is coupled into a second end of the yoke connector 502 such that sounds carried by the pneumatic tube 404 are coupled to the pneumatic port 106. Yoke clamps 504 may be used to secure the pneumatic tube 404 in the yoke connector 502.

The ear inserts 102 with the pneumatic ports 106 are inserted into the ear canals of the user. The adapter 506 may be inserted into the first end of the yoke connector 502 and the pneumatic tube 404 connected to the second end of the yoke connector and secured by the yoke clamps 504. The adapter/yoke connector assembly may then be positioned onto the pneumatic port 106.

Other embodiments are within the scope of the following claims.

What is claimed is:

[1. A magnetically inert headset comprising:

an ear insert having a through-hole and adapted to fit into an ear canal;

a pneumatic port disposed in the hole in the ear insert to receive audible sound waves and couple the sound waves to the ear canal;

a non-magnetic microphone coupled to the headset; and a stethoscope-type yoke, wherein the yoke includes pneumatic tubing acoustically coupled to both the pneumatic port and a non-magnetic transducer to couple the audible sound waves from the non-magnetic transducer.]

[2. The headset of claim 1 wherein the non-magnetic transducer comprises an audio transducer disposed in a magnet room of a magnetic resonance imaging system.]

[3. The headset of claim 1 wherein the non-magnetic transducer comprises a piezoelectric transducer.]

[4. The headset of claim 1 wherein the non-magnetic transducer comprises an electrostatic transducer.]

[5. A magnetically inert headset comprising:

an ear insert having a through-hole and adapted to fit into an ear canal;

a pneumatic port disposed in the hole in the ear insert to receive audible sound waves and couple the sound waves to the ear canal; and a stethoscope-type yoke, wherein the yoke includes pneumatic tubing acoustically coupled to both the pneumatic port and a non-magnetic transducer to couple the audible sound waves from the non-magnetic transducer.]

[6. The headset of claim 5 wherein the non-magnetic transducer comprises an audio transducer disposed in a magnet room of a magnetic resonance imaging system.]

[7. The headset of claim 5 wherein the non-magnetic transducer comprises a piezoelectric transducer.]

[8. The headset of claim 5 wherein the non-magnetic transducer comprises an electrostatic transducer.]

*9. A magnetically inert, noise-attenuating headset comprising:*

*an ear insert having a through-hole and adapted to fit into an ear canal;*

*a pneumatic port disposed in the hole in the ear insert to receive audible sound waves and couple the sound waves to the ear canal,*

*wherein the ear insert substantially conforms to the shape of the ear canal and is sized and composed of a material to attenuate noise created by a magnetic resonance imaging system by a sufficient extent as to enable a user undergoing examination by the system to hear sound waves through the pneumatic port;*

*a non-magnetic microphone coupled to the headset; and*

*a headset assembly, wherein the assembly includes pneumatic tubing acoustically coupled to both the pneumatic port and a non-magnetic transducer to couple the audible sound waves from the non-magnetic transducer.*

*10. A magnetically inert, noise-attenuating headset comprising:*

*an ear insert having a through-hole and adapted to fit into an ear canal;*

*a pneumatic port disposed in the hole in the ear insert to receive audible sound waves and couple the sound waves to the ear canal,*

*wherein the ear insert substantially conforms to the shape of the ear canal and is sized and composed of a material to attenuate noise created by a magnetic resonance imaging system by a sufficient extent as to enable a user undergoing examination by the system to hear sound waves through the pneumatic port; and*

*a headset assembly, wherein the assembly includes pneumatic tubing acoustically coupled to both the pneumatic port and a non-magnetic transducer to couple the audible sound waves from the non-magnetic transducer.*

*11. A magnetically inert, noise-attenuating headset comprising:*

*an ear insert having a through-hole and adapted to fit into an ear canal;*

*a pneumatic port disposed in the hole in the ear insert to receive audible sound waves and couple the sound waves to the ear canal,*

*wherein the pneumatic port and ear insert are arranged in combination to attenuate noise created by a magnetic resonance imaging system during operation of the system by a sufficient extent as to enable a user undergoing examination by the system to hear sound waves through the pneumatic port; and*

*a headset assembly, wherein the assembly includes pneumatic tubing acoustically coupled to both the pneumatic port and a non-magnetic transducer to couple the audible sound waves from the non-magnetic transducer.*

*12. The headset of claim 9, 10 or 11 wherein the headset assembly is a bi-aural headset assembly.*

*13. The headset of claim 9 or 10 wherein the pneumatic port and ear insert are arranged in combination to attenuate the noise produced by the magnetic resonance imaging system during operation of the magnetic resonance imaging system to enable the user undergoing examination by the system to hear sound waves through the pneumatic port.*

*14. The headset of claim 13 wherein the pneumatic port and ear insert are arranged in combination to attenuate noise produced by gradient coils of the magnetic resonance imaging system during operation of the magnetic resonance imaging system to enable the user undergoing examination by the system to hear sound waves through the pneumatic port.*

*15. The headset of claim 9, 10 or 11, wherein the ear insert is designed to be inserted into the ear canal to attenuate noise created by gradient coils of the magnetic resonance imaging system so as to enable the user undergoing examination by the system to hear sound waves through the pneumatic port.*

*16. The headset of claim 9, 10 or 11, wherein a substantial portion of the ear insert is designed to be inserted into the ear canal to attenuate noise created by gradient coils of the magnetic resonance imaging system so as to enable the user undergoing examination by the system to hear sound waves through the pneumatic port.*

*17. The headset of claim 9, 10 or 11, wherein the ear insert is designed to be fully inserted into the ear canal when the headset is in use.*

*18. The headset of claim 9 wherein the non-magnetic transducer comprises an audio transducer disposed in a magnet room of a magnetic resonance imaging system.*

*19. The headset of claim 9 wherein the non-magnetic transducer comprises a piezoelectric transducer.*

*20. The headset of claim 9 wherein the non-magnetic transducer comprises an electrostatic transducer.*

*21. The headset of claim 10 wherein the non-magnetic transducer comprises an audio transducer disposed in a magnet room of a magnetic resonance imaging system.*

*22. The headset of claim 10 wherein the non-magnetic transducer comprises a piezoelectric transducer.*

*23. The headset of claim 10 wherein the non-magnetic transducer comprises an electrostatic transducer.*

*24. The headset of claim 9, 10 or 11 wherein the ear insert is sized and shaped to be substantially fully fit within the ear canal.*

*25. The headset of claim 24 wherein the ear insert is sized and shaped to be fully fit within the ear canal.*

*26. The headset of claim 9, 10 or 11 wherein a portion of the ear insert to be placed within the ear canal is substantially cylindrical.*

*27. The headset of claim 9, 10 or 11 wherein an exterior shape of the surface of the ear insert configured to touch an inner surface of the ear canal, when the ear insert is in position for headset use, is approximately cylindrical or approximately tubular before insertion into the ear canal.*

*28. The headset of claim 9, 10 or 11 wherein an exterior shape of the surface of the ear insert configured to touch an inner surface of the ear canal, when the ear insert is in position for headset use, is cylindrical or tubular before insertion into the ear canal.*

*29. The headset of claim 9, 10 or 11 wherein the pneumatic port is configured to be positioned inside of the ear canal during operation of the headset.*

*30. The headset of claim 9, 10 or 11 wherein the pneumatic port extends through substantially the entire through-hole.*

*31. The headset of claim 9, 10 or 11 wherein the pneumatic port extends through substantially the entire ear insert.*

*32. The headset of claim 9, 10 or 11 further comprising an adapter to support the pneumatic port and to couple the pneumatic port to the pneumatic tubing.*

*33. The headset of claim 32 wherein the pneumatic port is retained or sealed in the adapter.*

*34. The headset of claim 32 wherein the adapter includes a gasket to retain or seal the pneumatic port in the adapter.*

*35. The headset of claim 9, 10 or 11 further comprising:*

*an adapter coupled to the pneumatic port; and*

*a connector coupled both to the adapter and to the pneumatic tube.*

*36. The headset of claim 35 wherein an end of the adapter fits into a first end of the connector, and a second end of the connector is coupled to the pneumatic tube.*

*37. The headset of claim 35 wherein the connector includes a right-angle bend.*

*38. The headset of claim 9, 10 or 11 wherein the headset is arranged to provide at least approximately 35 decibels of acoustic attenuation.*

*39. The headset of claim 9, 10 or 11 wherein the headset is arranged to provide a near-hermetic seal between the ear insert and an ear canal wall.*

*40. The headset of claim 9, 10 or 11 wherein the ear insert is an ear canal insert.*

*41. The headset of claim 9, 10 or 11 wherein the pneumatic port includes a hollow tube.*

*42. The headset of claim 9, 10 or 11 wherein the ear insert is made of compressible foam.*

*43. The headset of claim 9, 10 or 11 wherein the ear insert is made of compressible foam that fits fully within the ear canal.*

*44. The headset of claim 35 wherein the adapter includes a conical opening.*

*45. The headset of claim 9, 10 or 11 wherein the headset assembly comprises a stethoscope-type yoke.*

*46. The headset of claim 9 or 10 wherein the ear insert is sized and composed of a material to attenuate noise created by gradient coils of the magnetic resonance imaging system by a sufficient extent as to enable the user undergoing examination by the system to hear sound waves through the pneumatic port.*

*47. The headset of claim 11, wherein the pneumatic port and ear insert are arranged in combination to attenuate noise created by gradient coils of the magnetic resonance imaging system by a sufficient extent as to enable the user undergoing examination by the system to hear sound waves through the pneumatic port.*

* * * * *